United States Patent [19]

Siegfried et al.

[11] Patent Number: 5,262,402
[45] Date of Patent: Nov. 16, 1993

[54] PROCESS FOR PREPARING PYRIMIDINETRIONE DERIVATIVES

[75] Inventors: Bernard Siegfried, Douvaine, France; Jindrich Vachta; Karel Valter, both of Geneva, Switzerland; Stephane Hugentobler, Onex, Switzerland

[73] Assignee: Sapos S.A., Geneva, Switzerland

[21] Appl. No.: 768,852

[22] PCT Filed: Feb. 5, 1991

[86] PCT No.: PCT/EP91/00253
§ 371 Date: Oct. 30, 1991
§ 102(e) Date: Oct. 30, 1991

[87] PCT Pub. No.: WO91/12244
PCT Pub. Date: Aug. 22, 1991

[30] Foreign Application Priority Data

Feb. 8, 1990 [GB] United Kingdom ............... 9002890

[51] Int. Cl.$^5$ ............... A61K 31/675; A61K 31/515; C07D 239/02; C07F 9/02
[52] U.S. Cl. ............... 514/86; 514/270; 544/243; 544/299; 544/301; 544/302
[58] Field of Search ............... 544/299, 243, 302, 301; 514/270, 86

[56] References Cited

U.S. PATENT DOCUMENTS

| 814,496 | 3/1906 | Wolfes | 544/299 |
| 2,051,846 | 8/1936 | Holbig et al. | 544/299 |
| 2,161,212 | 6/1939 | Whitmore | 544/299 |
| 2,876,225 | 3/1959 | Donnison | 544/299 |

FOREIGN PATENT DOCUMENTS 125046 11/1984 European Pat. Off. .
2424262 11/1979 France .

*Primary Examiner*—Cecilia Tsang
*Attorney, Agent, or Firm*—Bacon & Thomas

[57] ABSTRACT

This invention relates to a process for preparation of pyrimidinetriones. It also relates to novel N-dihydroxyphosphoryl pyrimidinetrione derivatives which may be useful as water-soluble prodrugs of certain pyrimidinetrione compounds.

12 Claims, No Drawings

PROCESS FOR PREPARING PYRIMIDINETRIONE DERIVATIVES

This invention relates to a process for preparing pyrimidinetrione derivatives. It also relates to novel N-dihydroxyphosphoryl pyrimidinetrione derivatives which may be useful as water-soluble prodrugs of certain pyrimidinetrione compounds.

The compound, 1-(3-n-butoxy-2-carbamoyloxy-propyl)-5-ethyl-5-phenyl-(1H,3H,5H) pyrimidine-2,4,6-trione known as and hereinafter called febarbamate has previously been prepared and described—see for example Helvetica Chimica Acta, XLIV, pp. 105–113, 1960, and British Patent Specifications No. 1 581 834 and No. 2 137 999. These publications also describe related compounds and their preparation. The method of preparation has always involved the alkylation of a 5,5-disubstituted pyrimidinetrione by forming the sodium salt of the appropriate malonyl urea derivative and reacting this with an alkylating agent corresponding to the compound it is desired to prepare—generally a 1-halo-2-carbamoyloxy-3-alkoxy propane, and usually the chloro-compound. Such a process always provides a mixture of unchanged starting material, the N'-monosubstituted 5,5-disubstituted pyrimidinetrione derivative and the N,N'-disubstituted 5,5-disubstituted pyrimidinetrione derivative.

Such derivatives are described in the British Patent Specification No. 1 193 438. The reaction, being carried out in a heterogenous, highly viscous mass, is however difficult to handle and a considerable amount of the starting material 1-halo-2-carbamoyloxy-3-alkoxy propane is consumed in the unavoidable formation of unwanted N,N'-disubstituted derivative. This starting material is not easy to obtain, is time-consuming and difficult to prepare, and even despite rigorous purification always contains about 2% of the isomeric 1-halo-2-alkoxy-3-carbamoyloxy propane.

We have now devised an alternative process which enables the production of a substantially uncontaminated product. In addition our new procedures provide significant improvements in economy and ease of manipulation in the production of febarbamate and its derivatives.

According to one aspect of the invention we provide a process for the preparation of a compound of a formula (I)

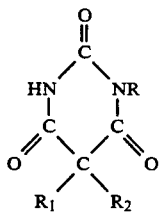

wherein $R_1$ and $R_2$, which may be the same or different, represent aliphatic, araliphatic or aryl groups, and R represents a group $-CH_2CH(OCONH_2)-C_2OX$ in which X is a $C_{1-5}$ alkyl group, which comprises reacting a compound of formula (II)

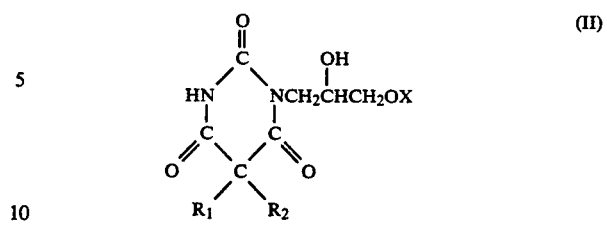

wherein $R_1$ and $R_2$ and X are as defined above with a dihalophosphinyl or halosulphonyl isocyanate to obtain a compound of formula (III)

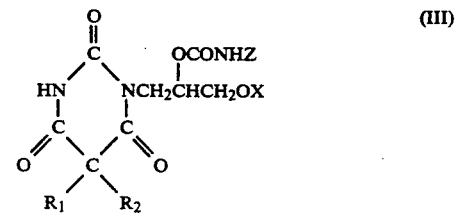

wherein $R_1$ and $R_2$ and X are as defined above and Z is a group of formula $-SO_2Y$ or $-POY_2$ wherein Y is a halogen atom, followed by hydrolysis of the compound of formula (III).

The intermediate compounds of formula (III) are believed novel, comprise a further feature of the invention, and may either be isolated, or may be hydrolysed in situ to provide compounds of formula (I) as defined above. Preferably, Y is a chlorine atom.

The reaction of the compounds of the formula (II) with a dihalophosphinyl or a halosulphonyl isocyanate may be carried out in solution, preferably in an anhydrous organic solvent, desirably an aromatic hydrocarbon such as toluene or a halogenated hydrocarbon such as methylene chloride, using substantially equimolar amounts of the reactants at a temperature between $-10°$ to $50°$. The complete reaction generally requires 1 to 5 hours, typically 1 hour at room temperature.

In the case of N-dihalophosphinyl derivatives the hydrolysis reaction may conveniently be conducted in a mixture of solvents, preferably an organic hydrocarbon solvent, such as toluene or cyclohexane, and water at pH 4 to 6 and at a temperature in the range $40°$ C. to $110°$ C., typically at about $70°$ C. The reaction time varies strongly depending on the conditions used from 1 to 24 hours, but typically about 6 hours at a pH of about 5.5 and at about $70°$ C. are required.

In the case of N-halosulphonyl derivatives the hydrolysis is more rapid, and is typically complete in about 1 hour at about $40°$ C.

We have found that the presence of a chlorinated organic solvent, such as methylene chloride or chloroform, inhibits splitting of N-P bonds and that further intermediates, believed novel, of formula (IV)

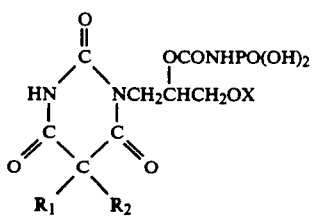

wherein $R_1$, $R_2$ and X are as defined above, can be isolated in good yield. In contrast to the compounds of the formula (I) these substances are readily soluble in water, especially in the form of their salts. Such compounds of formula (IV) comprise a further aspect of the invention. Isolated compounds of formula (IV) may be converted into compounds of formula (I) by the addition of water under conditions as described above for the hydrolysis of the N-dihalophosphinyl derivatives.

The compounds according to the invention may be formulated for administration as pro-drugs in any convenient way, but with particular advantage for injection and controlled-release compositions. The active ingredient may be presented in a powder form in ampoules or in other sterile containers and dissolved in a suitable sterile solvent shortly before use.

The particular properties of these compounds according to the invention may also be used to formulate controlled-release compositions in the form of partially soluble salts or absorbed on resins or in any other form known in the art. Suitable pharmaceutically acceptable diluents or excipients may be selected with ease by anyone skilled in the art.

The compounds of the formula (II) have been described as being prepared (Helvetica Chimica Acta, XLIV, pp. 105-113, 1960) by reaction of 5,5-disubstituted malonyl urea sodium salt with 1-chloro--2-hydroxy-3-alkoxy propane. The procedure described is highly laborious and quite impractical on a commercial scale in view of the heating times involved and the need to distil several times under reduced pressure to obtain a product of suitable purity. It will be realised that the preparation described in this reference provides a mixture of products, and the yields obtained were on the low side.

We have now also been able to devise a process for preparing the compounds of formula (II) which avoids many of the problems associated with the earlier procedure, and which provides a product which enables avoidance of problems in subsequent procedures.

According to a further aspect of the invention, we provide a process for the preparation of the compounds of formula (II) as defined above which comprises reacting a compound of formula (V)

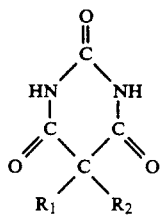

wherein $R_1$ and $R_2$ are as defined above with a compound of formula (VI) or (VIa)

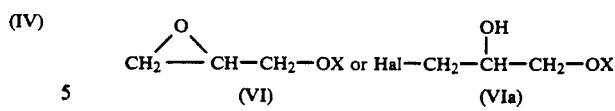

wherein X is as defined above and Hal is a halogen atom in the presence of approximately 0.01 to 0.1 molar equivalents of an organic base when a compound of formula (VI) is used, or approximately 1.0 molar equivalents of an organic base when a compound of formula (VIa) is used.

The base used will most desirably be selected so as to possess a pkB higher than about 10 in water. In addition, by selection of an organic base that will act also as a solvent for the reaction, or at least assist solubilisation of the reagents, a much smoother reaction in a homogeneous medium can be carried out which has significant handling advantages on a commercial plant scale. Preferred as bases are aliphatic, araliphatic or aromatic amines optionally substituted by hydroxyl or further amino groups, the trialkylamines, and particularly triethylamine being most preferred.

Reaction will desirably be carried out in a protic organic solvent such as a lower alkanol, e.g. ethanol or n-butanol, or an aprotic solvent such as an amide, e.g. dimethylformamide or dimethylacetamide, or those described above which may also comprise a suitable base, or in any suitable mixture thereof.

The temperature employed in this reaction will generally be in the range 20°-150° C., preferably 70° C., and a reaction time of from 2-48 hours is required, preferably 6 hours.

The compounds of formula (II) obtained may be isolated from the reaction mixture by methods described in British Patent Specification No. 1581834.

As a yet further advantage of this procedure, we have found that by varying the proportion of free barbituric acid starting material relative to the amount of alkylating agent, the proportion of N-monosubstituted product may be substantially improved, at the expense of the undesired N,N-disubstituted product. It is preferred to use an excess of barbituric acid starting material, from a molar ratio of at least 1:1 up to 3:1 of barbituric acid starting material: alkylating agent, preferably 1:1 to 2:1.

In a most preferred embodiment, we provide an overall process for the preparation of compounds of formula (I) above which comprises using the compounds of formulae (V) and (VI) as starting materials, and in which each of the process stages described above via compounds of formulae (II) and (III) is used sequentially.

The whole process is particularly well suited to a large-scale production of febarbamate (the compound of formula (I) in which $R_1$ is ethyl, $R_2$ is phenyl and R is a 3-n-butoxy-2-carbamoyloxypropyl group) and its derivatives using only very classical operations such as extractions, crystallizations, filtrations and evaporations.

The various aspects and embodiments of the invention will now be described and further illustrated in the following non-limiting Examples.

EXAMPLES

EXAMPLE 1

1-(3-n-Butoxy-2-hydroxypropyl)-5-ethyl-5-phenyl-(1H,3H,5H)-pyrimidine-2,4,6-trione A solution of phenobarbital (69.6 g, 0.3 mole) in ethanol (150 ml) containing triethylamine (2.02 g, 0.02 mole) was stirred with butyl glycidyl ether (26.0 g, 0.2 mole) (available from Merck & Co.) for 6 hours at 70° C. The reaction mixture was then poured into water (500 ml) and the precipitated product was extracted with toluene (200 ml) at 70° C. The toluene layer was separated, washed with 3% aqueous sulphuric acid (200 ml) and left overnight at 4° C. The precipitated phenobarbital was filtered off and the filtrate extracted with 5% aqueous sodium carbonate (5×100 ml). The organic layer was then extracted with 1M aqueous sodium hydroxide (2×200 ml), the aqueous layers collected, washed with toluene (100 ml) and the pH was adjusted to 3 with sulphuric acid. The precipitated product was extracted with toluene (150 ml), the organic layer was separated, dried and evaporated under reduced pressure to give the title compound (40.1 g, 55%); purity by HPLC 99% m.p. 92° C.

EXAMPLE 2

1-(3-n-Butoxy-2-hydroxypropyl)-5-ethyl-5-phenyl-(1H,3H,5H)-pyrimidine-2,4,6-trione A solution of phenobarbital (69.6 g, 0.3 mole) in dimethylformamide (60 ml) containing triethylamine (20.2 g, 0.2 mole) was stirred with 1-chloro-3-n-butoxy-2-propanol (33.2 g, 0.2 mole) for 6 hours at 70° C. The reaction mixture was then poured into 3% sulphuric acid (500 ml) and the precipitated product was extracted with toluene (200 ml) at 70° C. The toluene layer was separated, washed with 3% aqueous sulphuric acid (200 ml) and left overnight at 4° C. The precipitated phenobarbital was filtered off and filtrate extracted with 5% aqueous sodium carbonate (5×100 ml). The organic layer was then extracted with 1M aqueous sodium hydroxide (2×200 ml), the aqueous layers collected, washed with toluene (100 ml) and the pH was adjusted to 3 with sulphuric acid. The precipitated product was extracted with toluene (150 ml), the organic layer was separated, dried and evaporated under reduced pressure to give the title compound (38.5 g, 53%); purity by HPLC 96.5%.

EXAMPLE 3

Febarbamate

A solution of 1-(3-n-butoxy-2-hydroxypropyl)-5-ethyl-5-phenyl-(1H,3H,5H)-pyrimidine-2,4,6-trione (10.83 g, 0.03 mole) in 20 ml of methylene chloride was added dropwise into a stirred solution of chlorosulphonyl isocyanate (4.65 g, 0.033 mole) in 20 ml of methylene chloride at a temperature below 30° C. The reaction mixture was stirred for 1 hour at room temperature and then ice-cold water (100 ml) was added. After a vigorous reaction had ceased the reaction mixture was heated for 1 hour at 40° C.

The organic layer was then separated, washed with water (2×100 ml), dried and evaporated to give the title compound (11.2 g, 92.4%) as a vitreous solid, containing 3% of the starting compound (by HPLC). The product was recrystallised from acetonitrile to yield the febarbamate (8.5 g, 70.1%), m.p. 104° C. Purity 99.0% at least.

EXAMPLE 4

Febarbamate

A solution of 1-(3-n-butoxy-2-hydroxypropyl)-5-ethyl-5-phenyl-(1H,3H,5H)-pyrimidine-2,4,6-trione (10.83 g, 0.03 mole) in toluene (20 ml) of was added dropwise into a stirred solution of dichlorophosphinyl isocyanate (5.3 g, 0.033 mole) in toluene (20 ml) at a temperature below 30° C.

The reaction mixture was stirred for 1 hour at room temperature and then ice-cold water (100 ml) was added. After a vigorous reaction had ceased the pH of the solution was adjusted to 5 using a solution of sodium hydroxide.

The reaction mixture was then stirred at 70° C. for 6 hours, cooled, the organic phase separated, washed with water (3×50 ml) dried and evaporated to yield the title compound (10.8 g, 89%) as a glassy solid, containing approx. 3% of the starting product (by HPLC).

Recrystallisation from acetonitrile gave the febarbamate (8.1 g, 66.8%), m.p. 104° C. Purity at least 99.0%.

EXAMPLE 5

1-[3-n-Butoxy-2-(N-dihydroxyphosphoryl)-carbamoyloxypropyl]-5-ethyl-5-phenyl-(1H,3H,5H)-pyrimidine-2,4,6-trione, (Febarbamate N-phosphoric acid)

A solution of 1-(3-n-butoxy-2-hydroxypropyl)-5-ethyl-5-phenyl-(1H,3H,5H)-pyrimidine-2,4,6-trione (10.83 g, 0.03 mole) in methylene chloride (20 ml) of was added dropwise into a stirred solution of dichlorophosphinyl isocyanate (5.3 g, 0.033 mole) in methylene chloride (20 ml). The temperature was kept below 30° C. The reaction mixture was stirred at room temperature for 1 hour and then ice-cold water (100 ml) was added. This mixture was stirred vigorously for 1 hour and partially evaporated under reduced pressure The precipitated oil was extracted with ether (2×50 ml), the organic layer separated, washed with water (2×200 ml) dried and then evaporated to yield the title compound (11.3 g, 85%); purity by HPLC 95%.

IR: 3239 (broad), 2963, 2877, 1756, 1739, 1697, 1443, 1367, 1207, 1109, 1032, 950, 892, 820, 776, 722, 695, 557 cm$^{-1}$ (KBr disc).

EXAMPLE 6

Febarbamate

A solution of febarbamate N-phosphoric acid (5 g, 0.0113 mole) in water (50 ml) was layered with toluene (25 ml) and the pH adjusted to 5.5 using a solution of sodium carbonate. The mixture was vigorously stirred for 6 hours at 70° C. The organic layer was separated, washed with water (2×25 ml), dried and evaporated to give febarbamate (3.8 g, 93%); purity by HPLC 97.5%.

EXAMPLE 7

1-(3-n-butoxy-2-hydroxypropyl)-5,5-dipropyl-(1H,3H,5H)pyrimidine-2,4,6-trione

A solution of 5,5 dipropyl-(1H,3H,5H)-pyrimidine-2,4,6-trione (30.8 g, 0.15 mole) in dimethylformamide (30 ml) containing triethylamine (2.02 g, 0.2 mole) was mixed with butyl glycidyl ether (13 g, 0.1 mole). The mixture was heated at 60° C. for 6 hours. The solution was then diluted with water (150 ml) and extracted with toluene (2×50 ml). The organic layer was separated, washed with water (2×100 ml) dried and extracted with 5% aqueous sodium carbonate (6×100 ml). The toluene phase was then extracted with 1M aqueous sodium hydroxide (2×100 ml), the aqueous layers separated, washed with toluene (100 ml) and the pH was adjusted to 3 with sulphuric acid. The precipitated oily product was extracted with toluene (100 ml), and the organic layer was separated, washed with water, dried and evaporated to yield the title compound (16.3 g; 51.6%); purity by HPLC 96.5%.

EXAMPLE 8

1-(3-n-Butoxy-2-(N-dihydroxyphosphoryl)carbamoyloxypropyl)-5,5-dipropyl-(1H,3H,5H)-pyrimidine-2,4,6-trione A solution of 1-(3-n-butoxy-2-hydroxy-propyl)-5,5-dipropyl-(1H,3H,5H)-pyrimidine-2,4,5-trione (12.52 mg, 0.04 mole) in methylene chloride (20 ml) was added dropwise into a stirred solution of dichlorophosphorinyl isocyanate (7 g, 0.044 mole) in methylene chloride (20 ml) at a temperature below 30° C. The reaction mixture was stirred at room temperature for 1 hour and then cold water (100 ml) was added. This mixture was then stirred vigorously for 1 hour, partially evaporated under reduced pressure and the precipitated oil was extracted with ether. The organic layer was separated, washed with water (20 ml), dried and evaporated to give the title compound as a glassy solid (12.8 g; 81.%); purity by HPLC 95.5%.

IR: 3247 (broad), 2968, 2935, 2877, 1752, 1722, 1694, 1443, 1356, 1207, 1104, 1055, 1024, 950, 881, 820, 776, 692, 497, cm$^{-1}$ (KBr disc).

EXAMPLE 9

1-(3-n-Butoxy-2-carbamoyloxypropyl)-5,5-dipropyl(1H,3H,5H)-pyrimidine-2,4,6-trione A solution of 1-(3-n-butoxy-2-(N-dihydroxyphosphoryl)carbamoyloxypropyl)-5,5-dipropyl-(1H,3H,5H)-pyrimidine-2,4,6-trione (10 g, 0.0254 mole) in water (75 ml) was layered with toluene (25 ml) and the pH adjusted to 5.5 using a solution of sodium carbonate. The reaction mixture was then vigorously stirred for 6 hours at 70° C., the organic layer separated, washed with water (2×25 ml), dried and evaporated to yield the title compound (8.2 g, 90%); purify 94% (by HPLC). Crystallization in methanol gave 6.8 g (7.6%) of the product; m.p. 10° C.

EXAMPLE 10

Disodium febarbamate N-phosphate

A solution of febarbamate N-phosphoric acid (4.4 g, 0.01 mole) and sodium hydroxide (0.8 g, 0.02 mole) in methanol (20 ml) was evaporated under reduced pressure (bath temperature 30° C.). The residue was crystallized from anhydrous methanol (4 ml) to give the title product (2.2. g, 47%), m.p. 136°-138° C.

We claim:

1. A process for the preparation of a compound of a formula (I)

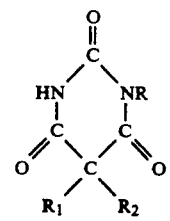

wherein $R_1$ and $R_2$, which may be the same or different, represent $C_{1-5}$ alkyl or phenyl, and R represents a group —$CH_2CH(OCONH_2)$—$CH_2OX$ in which X is a $C_{1-5}$ alkyl group, which comprises reacting a compound of formula (II)

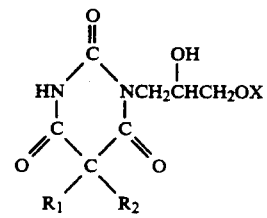

wherein $R_1$ and $R_2$ and X are as defined above with a dihalophosphinyl or halosulphonyl isocyanate to obtain a compound of formula (III)

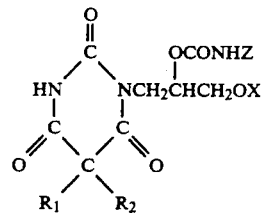

wherein $R_1$ and $R_2$ and X are as defined above and Z is a group of formula —$SO_2Y$ or —$POY_2$ wherein Y is a halogen atom followed by hydrolysis of the compound of formula (III).

2. A process according to claim 1 in which a compound of formula (II) is reacted with a dihalophosphinyl isocyanate wherein the product is initially hydrolysed in the presence of a mixture of water and chlorinated organic solvent to produce a compound of formula (IV)

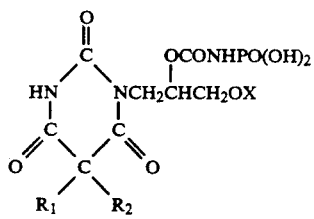

wherein $R_1$, $R_2$ and X are as defined above, followed by further hydrolysis to yield the compound of formula (I).

3. A process according to claim 1 wherein Y is a chlorine atom.

4. A compound of formula (III)

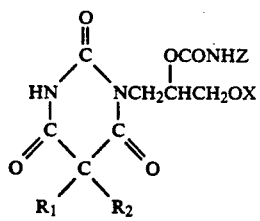

(III)

wherein $R_1$ and $R_2$, which may be the same or different, represent $C_{1-5}$alkyl or phenyl, X is $C_{1-5}$alkyl, and Z is a group of formula $-SO_2Y$ or $-POY_2$ wherein Y is a halogen atom.

5. A compound of formula (IV)

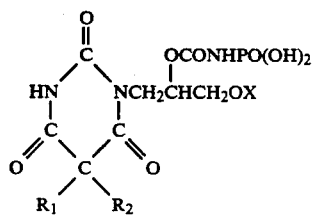

(IV)

wherein $R_1$ and $R_2$, which may be the same or different, represent $C_{1-5}$alkyl or phenyl, and X is $C_{1-5}$alkyl or a pharmaceutically acceptable salt thereof.

6. A pharmaceutical composition for use as a pro-drug which comprises a pro-drug effective amount of a compound of formula (IV) as defined in claim 5 or a pharmaceutically acceptable salt thereof in admixture with a pharmaceutically acceptable carrier, excipient or diluent.

7. A process of the preparation of a compound of formula (II) as defined in claim 1 which comprises reacting a compound of formula (V)

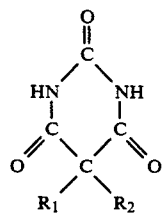

(V)

wherein $R_1$, and $R_2$ are as defined in claim 1 with a compound of formula (VI) or (VIa)

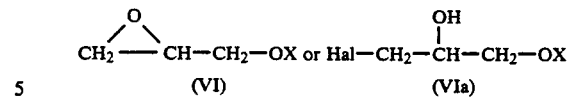

wherein X is as defined in claim 1 and Hal is a halogen atom in the presence of approximately 0.01 to 0.1 molar equivalents of an organic base when a compound of formula (VI) is used, or approximately 1.0 molar equivalents of an organic base when a compound of formula (VIa) is used, and wherein the organic base has a $pK_B$ higher than about 10 in water.

8. A process according to claim 7 wherein the molar ratio of compound of formula (V) to compound of formula (VI) or (VIa) is in the range 1:1 to 3:1.

9. A process according to claim 1 for the preparation of febarbamate, wherein the starting material of formula (II) is prepared by reacting a compound of formula (V)

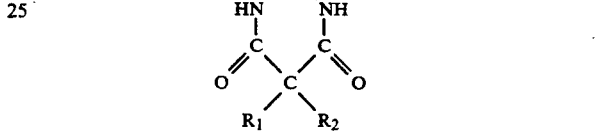

wherein $R_1$ and $R_2$ are as defined in claim 1 with a compound of formula (VI) or (VIa):

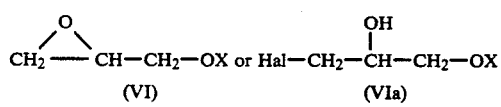

wherein X is as defined in claim 1 and Hal is a halogen atom in the presence of approximately 0.01 to 0.1 molar equivalents of an organic base when a compound of formula (VI) is used, or approximately 1.0 molar equivalents of an organic base when a compound of formula (VIa) is used, and wherein the organic base has a $pK_B$ higher than about 10 in water.

10. A process according to claim 2 wherein Y is a chlorine atom.

11. A process according to claim 7 wherein the organic base is a trialkylamine.

12. A process according to claim 9 wherein the organic base is a trialkylamine.

* * * * *